(12) United States Patent
Widu

(10) Patent No.: US 10,004,573 B2
(45) Date of Patent: Jun. 26, 2018

(54) GUIDANCE ELEMENT FOR A TOOTH

(71) Applicant: Friedrich Widu, Erding (DE)

(72) Inventor: Friedrich Widu, Erding (DE)

(*) Notice: Subject to any disclaimer, the term of this patent is extended or adjusted under 35 U.S.C. 154(b) by 0 days. days.

(21) Appl. No.: 14/136,479

(22) Filed: Dec. 20, 2013

(65) Prior Publication Data

US 2014/0178830 A1  Jun. 26, 2014

(30) Foreign Application Priority Data

Dec. 21, 2012 (DE) .......................... 10 2012 224 328

(51) Int. Cl.
*A61C 7/08* (2006.01)
*A61C 7/12* (2006.01)
*A61C 7/14* (2006.01)
*A61C 7/30* (2006.01)

(52) U.S. Cl.
CPC .................. *A61C 7/08* (2013.01); *A61C 7/12* (2013.01); *A61C 7/143* (2013.01); *A61C 7/30* (2013.01)

(58) Field of Classification Search
CPC .. A61C 7/146; A61C 7/00; A61C 7/02; A61C 7/08; A61C 7/12; A61C 7/125; A61C 7/14; A61C 7/20; A61C 7/28; A61C 7/143; A61C 7/30
USPC ....................................................... 433/8–16
See application file for complete search history.

(56) References Cited

U.S. PATENT DOCUMENTS

| 3,775,850 | A | * | 12/1973 | Northcutt | 433/16 |
| 4,330,273 | A | * | 5/1982 | Kesling | 433/5 |
| 4,371,337 | A | * | 2/1983 | Pletcher | 433/10 |
| 4,856,991 | A | * | 8/1989 | Breads et al. | 433/6 |
| 4,880,380 | A | * | 11/1989 | Martz | 433/11 |
| 5,067,896 | A | * | 11/1991 | Korn | 433/6 |
| 5,186,623 | A | * | 2/1993 | Breads et al. | 433/6 |
| 5,975,893 | A | * | 11/1999 | Chishti et al. | 433/6 |
| 6,299,440 | B1 | * | 10/2001 | Phan et al. | 433/24 |
| 6,309,215 | B1 | * | 10/2001 | Phan et al. | 433/24 |
| 7,059,850 | B1 | * | 6/2006 | Phan et al. | 433/24 |
| 8,356,993 | B1 | * | 1/2013 | Marston | 433/24 |
| 2002/0106604 | A1 | * | 8/2002 | Phan et al. | 433/24 |
| 2003/0198911 | A1 | * | 10/2003 | Knopp et al. | 433/6 |
| 2003/0207224 | A1 | * | 11/2003 | Lotte | 433/6 |
| 2004/0009449 | A1 | * | 1/2004 | Mah et al. | 433/7 |
| 2004/0229183 | A1 | * | 11/2004 | Knopp et al. | 433/6 |
| 2005/0233276 | A1 | | 10/2005 | Kopelman et al. | |
| 2006/0099544 | A1 | * | 5/2006 | Lai et al. | 433/6 |
| 2006/0115785 | A1 | * | 6/2006 | Li et al. | 433/80 |
| 2006/0223022 | A1 | * | 10/2006 | Solomon | 433/6 |
| 2009/0280450 | A1 | * | 11/2009 | Kuo | 433/9 |

(Continued)

FOREIGN PATENT DOCUMENTS

| DE | 102010008749 | 8/2011 |
| JP | 2008-68113 | 3/2008 |
| WO | WO 2011/102994 | 8/2011 |

*Primary Examiner* — Cris L Rodriguez
*Assistant Examiner* — Hao D Mai
(74) *Attorney, Agent, or Firm* — Greer, Burns & Crain, Ltd.; Steve P. Fallon

(57) ABSTRACT

Guidance element for a tooth for interacting with an orthodontic treatment splint, the guidance element having a tooth connection surface as well as at least one engagement surface for engagement in the treatment splint in order to exert orthodontic torques and/or forces onto the tooth during the engagement, and having at least one slot for reception of an orthodontic treatment arch.

28 Claims, 15 Drawing Sheets

(56) References Cited

U.S. PATENT DOCUMENTS

| | | | |
|---|---|---|---|
| 2010/0279245 A1* | 11/2010 | Navarro | 433/6 |
| 2011/0129786 A1* | 6/2011 | Chun et al. | 433/19 |
| 2011/0269091 A1 | 11/2011 | Li et al. | |
| 2013/0029283 A1* | 1/2013 | Matty | A61C 7/002 |
| | | | 433/3 |

* cited by examiner

US 10,004,573 B2

GUIDANCE ELEMENT FOR A TOOTH

PRIORITY CLAIM

This application claims priority under 35 U.S.C. 119 from prior German Patent Application Number 10 2012 224 328.3, which was filed on Dec. 21, 2012.

FIELD

The invention relates to a guidance element for a tooth as well as to a set of guidance elements having a corresponding orthodontic treatment splint.

BACKGROUND

For the orthodontic treatment of patients there are inter alia the following two alternatives:

In a first alternative having fixed braces brackets are glued onto the teeth of the patient which are to be treated and connected to one another by an orthodontic wire. The brackets have a pad for connection to the tooth and a bracketbody having a slot which receives the archwire. The brackets can be arranged buccally or lingually.

In a second alternative, small guidance elements are glued onto the teeth of the patient which are to be treated. The patient receives a corresponding treatment splint into which the patient "bites", whereby the guidance elements on the teeth engage with correspondingly assigned guiding pockets in the treatment splint. The guiding pockets are arranged in the treatment splint such that they exert the desired orthodontic forces and/or torques onto the teeth via the guidance elements.

Generally, in this alternative the complete orthodontic treatment of the patient is planned at the computer by means of a software, i.e. an existing initial situation is converted into a desired target situation: for that purpose the guidance elements, for example from a predefined library of guidance elements, are arranged on the teeth which are to be treated. Subsequently, different treatment stages are defined within which certain partial steps of the treatment shall be achieved. For each of these treatment stages a treatment splint is calculated and produced subsequently. If treatments are necessary in the upper and in the lower jaw, the patient receives the necessary treatment splints for the upper and for the lower jaw for each treatment step. After completion of a treatment stage the patient exchanges the treatment splint, i.e. he exchanges the "old" for the "new" treatment splint, until the treatment is completed. Usually, in this treatment which is also called aligner therapy as a rule 20 treatment stages are defined, wherein a lower or higher number of stages is possible, too, though.

It is a disadvantage of the first alternative that with buccal brackets it is optically not attractive and also involves a high hygienic effort on the side of the patient.

A disadvantage of the second alternative is that certain treatment steps, for example the rotation or angulation or extrusion of a tooth, can be carried out only difficulty or not at all with the treatment splints.

SUMMARY OF THE INVENTION

A guidance element for a tooth for interacting with an orthodontic treatment splint is provided by the invention. The guidance element has a tooth connection surface and at least one engagement surface for engagement in the treatment splint in order to exert orthodontic torques and/or forces onto the tooth during the engagement, including at least one slot for reception of an orthodontic treatment arch.

BRIEF DESCRIPTION OF THE DRAWINGS

Further features, details and advantages of the invention unfold from the claims and from the following description of preferred embodiments as well as from the drawing. There are shown:

Figure 1:
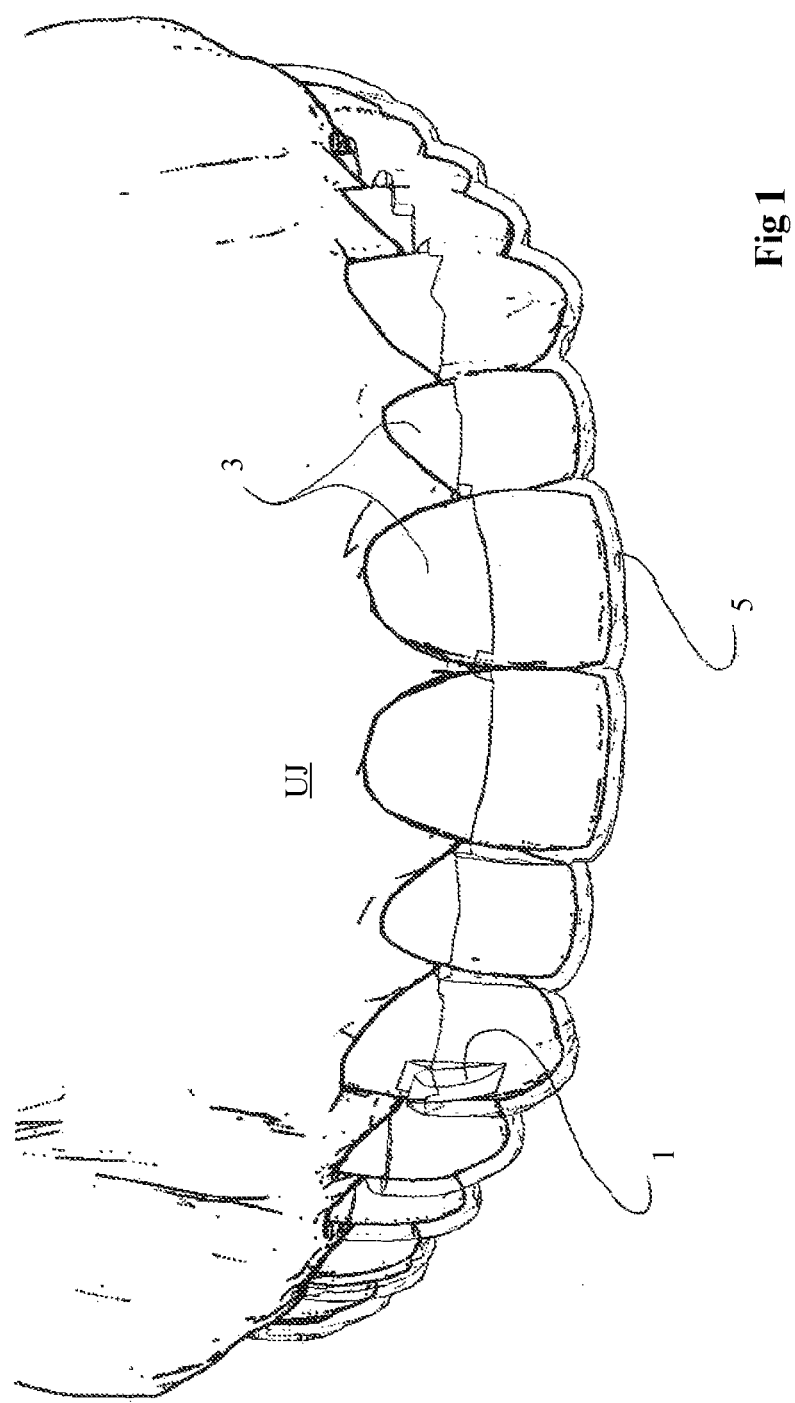
FIG. 1 a perspective view of an upper jaw of a patient, wherein guidance elements and a treatment splint are arranged on the teeth, FIG. 2 a) a top view, b) a perspective view, c) a first lateral view and d) a second lateral view of a guidance element according to the invention, FIG. 3 a) a top view, b) a perspective view, c) a first lateral view and d) a second lateral view of a guidance element according to the invention in a further embodiment, FIG. 4 a) a top view, b) a perspective view, c) a first lateral view and d) a second lateral view of a guidance element according to the invention in a further embodiment, FIG. 5 a) a top view, b) a perspective view, c) a first lateral view and d) a second lateral view of a guidance element according to the invention in a further embodiment, FIG. 6 a) a top view, b) a perspective view, c) a first lateral view and d) a second lateral view of a guidance element according to the invention in a further embodiment, FIG. 7 a) a top view, b) a perspective view, c) a first lateral view and d) a second lateral view of a guidance element according to the invention in a further embodiment, FIG. 8 a) a top view, b) a perspective view, c) a first lateral view and d) a second lateral view of a guidance element according to the invention in a further embodiment, FIG. 9 a) a top view, b) a perspective view, c) a first lateral view and d) a second lateral view of a guidance element according to the invention in a further embodiment, FIG. 10 a) a top view, b) a perspective view, c) a first lateral view and d) a second lateral view of a guidance element according to the invention in a further embodiment, FIG. 11 a) a top view, b) a perspective view, c) a first lateral view and d) a second lateral view of a guidance element according to the invention in a further embodiment, FIG. 12 a) a top view, b) a perspective view, c) a first lateral view and d) a second lateral view of a guidance element according to the invention in a further embodiment, FIG. 13 a perspective view of a guidance element in a further embodiment, FIG. 14 a) a top view, b) a perspective view, c) a first lateral view and d) a second lateral view of a guidance element according to the invention in a further embodiment, and FIG. 15 a) a top view, b) a perspective view, c) a lateral view of a guidance element according to the invention in a further embodiment.

DETAILED DESCRIPTION OF THE PREFERRED EMBODIMENTS a preferred guidance element according to the invention comprises at least one slot. By this at least one slot the guidance element has become a hybrid element: it can be used as a conventional guidance element in the course of a therapy using an aligner but also as a conventional standard bracket in the course of a therapy using standard brackets.

Usually, it will not be possible that the patient wears the treatment splint if an orthodontic treatment arch is ligated into the guidance elements as in this case the treatment splint would have to have free spaces for the treatment arch. In such a case the patient would wear the treatment splint until an exchange to the next treatment splint would fall due. Then, however, one would not change to the next treatment splint but an orthodontic treatment arch would be inserted in order to carry out the next treatment step therewith, for example the extrusion of a tooth. Only when this treatment step would be completed, the orthodontic treatment arch would be removed and it would be exchanged for the next treatment splint. Thus, by means of the guiding elements, either a treatment step would be carried out with the treatment splints or a treatment step would be carried out by means of an orthodontic treatment arch. Therein one can switch between these two treatment alternatives any number of times and there can also be carried out any number of steps of a treatment alternative successively before one switches again to the other treatment alternative. This gives a great freedom of treatment to the attending orthodontist.

In exceptional cases, however, it is possible to carry out both treatment alternatives simultaneously. If for example a treatment splint is arranged only over a portion of a jaw, for example over the left half of the lower jaw, a treatment using an orthodontic treatment arch could take place in the right half, for example the extrusion of a tooth. Further, it is also possible to shorten the treatment splint for example at a tooth in gingival-occlusal direction in order to arrange a guidance element for an extrusion there.

The at least one engagement surface can be a distal and/or a mesial and/or an occlusal engagement surface. In case the guidance element is a buccal or a lingual guidance element, the at least one engagement surface can also be or comprise, respectively, a buccal or a lingual engagement surface.

Advantageously, a guidance element has at least two and further preferred at least three slots.

Preferably, at least one of the at least one slot is self-ligating. However, it is also possible and lies within the scope of the invention that hooks or knobs or the like are provided at the guidance element in order to attach a ligation thereto for ligating an orthodontic treatment arch thereto.

Preferably, the guidance element at least partially consists of a ceramic material, a plastic material, for example PEAK, PEEK, PEKK, PEEK, PEKKTON, a metal, as for example gold, or an alloy and optionally at least partially has a coating, for example of teflon, in order to predefine or influence friction properties and/or corrosion properties.

Advantageously, at least one of the at least one slot has a circular, a square, a rectangular or a polygonal shape in the cross section.

A slot can be arranged within the guidance element centrally or gingivally or occlusally in occlusal-gingival direction.

Preferably, a shape and/or size of the tooth connection surface is adapted to a predefined tooth, for example to a canine or to an incisor.

Since the guidance element as hybrid element is supposed to be applicable as a standard bracket within a conventional standard bracket therapy, it can have any additional components which are known from standard brackets, as for example hook, wing, knob, tube or an undercut, for example in order to hook in a rubber strap.

Hence, for an orthodontic treatment of a patient a set of at least two guidance elements according to the invention as well as at least one corresponding treatment splint is necessary. Usually, one guidance element is required for each tooth of the jaw which is to be treated. However, it lies within the scope of the invention that not all but only a few teeth of a jaw, respectively, are provided with the guidance elements according to the invention.

The at least one required treatment splint can be a treatment splint for the upper jaw or one for the lower jaw. Usually, however, one treatment splint for the upper jaw and one for the lower jaw will be required, as in many cases a treatment of both jaws takes place.

Advantageously, multiple treatment splints for the upper jaw and/or for the lower jaw are provided for different treatment stages of an orthodontic treatment, respectively.

It is possible and lies within the scope of the invention that for at least one tooth of the patient several guidance elements are provided in order to simultaneously arrange them on the tooth in at least one treatment stage.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

In FIG. 1 a treatment situation of a patient is shown who is treated according to the aligner therapy described above, see above alternative 2. The teeth 3 of the upper jaw UJ engage in an orthodontic treatment splint 5, wherein for simplification only on one tooth 3 a guidance element 1 is arranged. The guidance element 1 is arranged on the buccal tooth surfaces of the teeth 3 and connected to these by a conventional glued connection. The type of the glued connection corresponds to the one that is used in the gluing of conventional brackets. By means of the guidance elements 1 a force is exerted from the treatment splint 5 onto the corresponding teeth 3, as described above.

In gingival-occlusal direction the treatment splint 5 has different heights: in the region of the molars it advances to the gingival edge, in the region of the canines it has only a small distance to the gingival edge and in the region of the incisors it advances approximately to the middle of the incisors.

Figure 2:
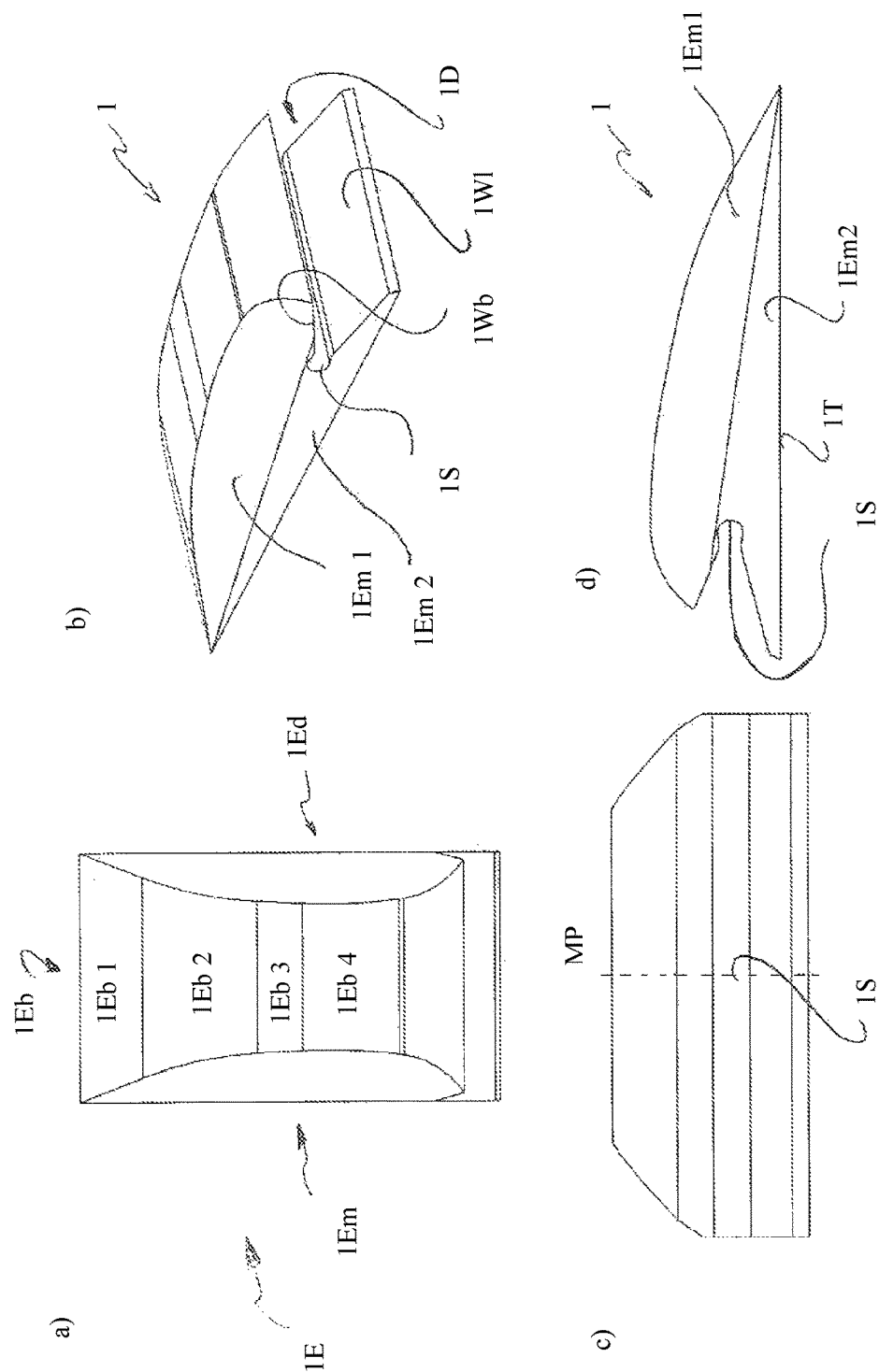

In FIG. 2 there is depicted in a) a top view, b) a perspective view, c) a first lateral view and d) a second lateral view of a guidance element 1 according to the invention.

The guidance element has engagement surfaces 1E opposite and facing away from the tooth connection surface by which it is in positive engagement with a guiding pocket of the treatment splint 5. For formation of the glued connection between the tooth 3 and the guidance element 1 the tooth connection surface 1T is provided by which the guidance element 1 is glued onto the buccal tooth surface of the tooth 3.

The guidance element 1 has a buccal engagement surface 1Eb which is divided into several sections 1Eb1, 1Eb2, 1Eb3 and 1Eb4, wherein these run at an angle to one another, respectively, see FIGS. 1a) and 1d). The sections 1Eb1 and 1Eb3 are flat, whereas the sections 1Eb2 and 1Eb4 form a convex curve towards buccal. This allows an easy sliding of the treatment splint 5 onto the teeth 3 and an easy removal of the same.

The guidance element 1 has a mesial and a distal engagement surface 1Em, 1Ed, wherein these, respectively, are divided into individual sections 1Em1, 1Em2, 1Ed1, 1Ed2. The engagement surfaces 1Em, 1Ed run symmetrically to a median plane MP running vertically in FIG. 2c). The sections 1Ed1, 1Em1 run at an angle to the median plane MP. The sections 1Ed2, 1Em2 run in parallel to the median plane MP.

Further, the guidance element 1 has a slot 1S in order to arrange an orthodontic treatment wire therein. In the present case, the slot 1S is an open slot and has a circular cross section and is arranged perpendicularly to the longitudinal axis of the guidance element 1. The guidance element 1 has an almost wedge-shaped wire insertion region 1W in order to allow an easy insertion of the orthodontic wire into the slot 15. The wire insertion region 1W also runs perpendicularly to the longitudinal axis of the guidance element 1 and comprises a buccal and a lingual wire insertion surface 1Wb, 1Wl.

The guidance element 1 and the slot 1S, respectively, is self-ligating: an orthodontic wire is inserted along and between the wire insertion surfaces 1Wb, 1Wl into the slot 1S, wherein the wire is deformed slightly at the narrowest site of the wire insertion region 1W. When the wire is arranged within the slot 1S it can only be removed again from the slot 1S by applying a corresponding gingivally directed force.

In the region of the guidance element 1 the treatment splint 5 is shortened in gingival-occlusal direction to such an extent that an orthodontic wire can be arranged within the slot 1S despite the engagement of the teeth 3 with the treatment splint 5, for example in order to carry out an extrusion, as described above.

The guidance element 1 is produced as one-piece and consists of a synthetic material, for example produced in a spray process or in a milling process.

Figure 3:
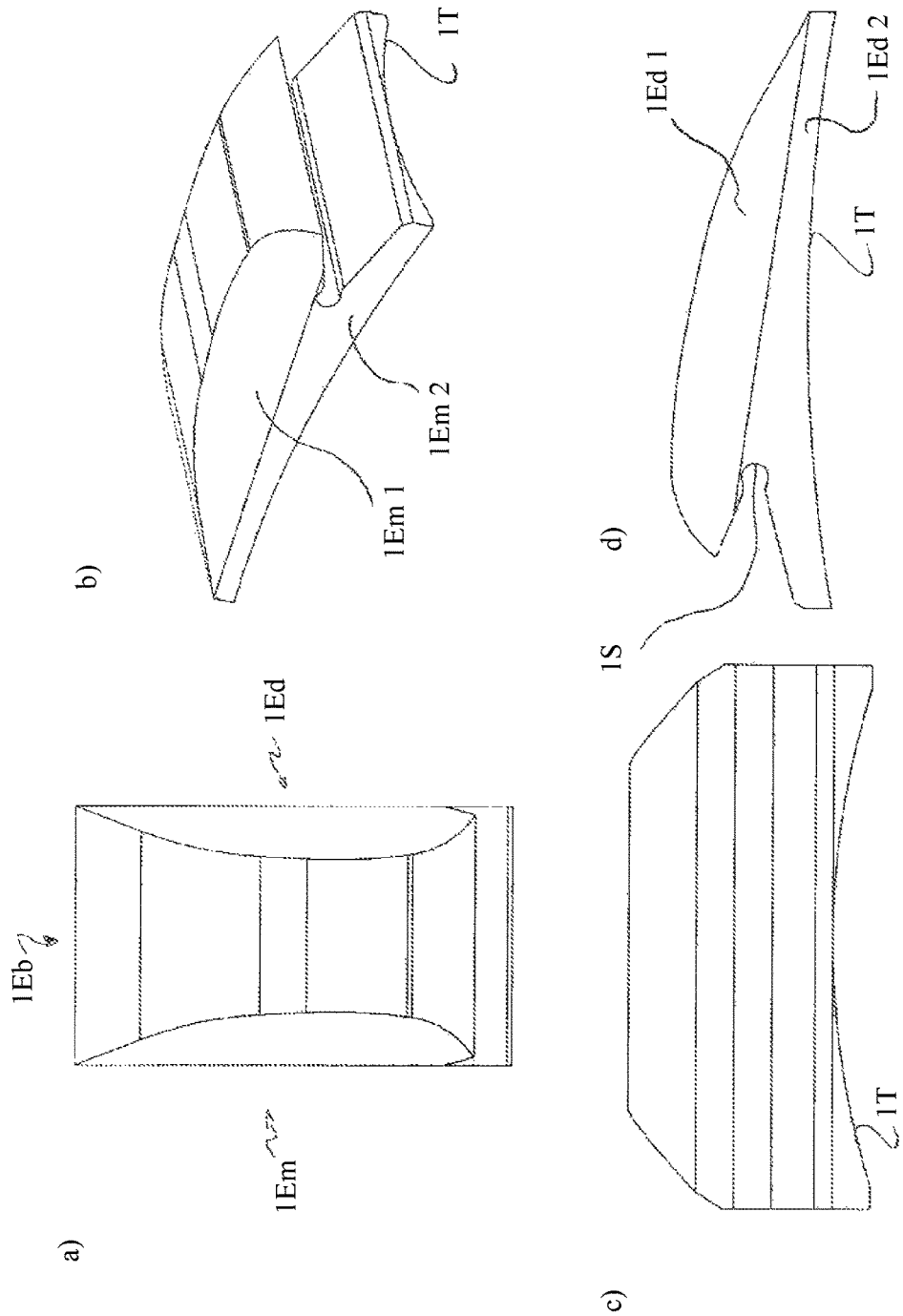

In FIG. 3 there is depicted in a) a top view, b) a perspective view, c) a first lateral view and d) a second lateral view of the guidance element 1 of FIG. 2 in a further embodiment. The embodiment of FIG. 3 differs from that of FIG. 2 in that the tooth connection surface 1T is not planar but is adapted to the buccal tooth surface of a tooth 3, in the present case only exemplarily to a 1st tooth of the upper jaw. In FIG. 3*c*) a curvature of the tooth connection surface 1T around a gingival-occlusal axis is discernible. In FIG. 3*d*) a curvature of the tooth connection surface 1T around a mesio-distal axis is discernible.

Figure 4:
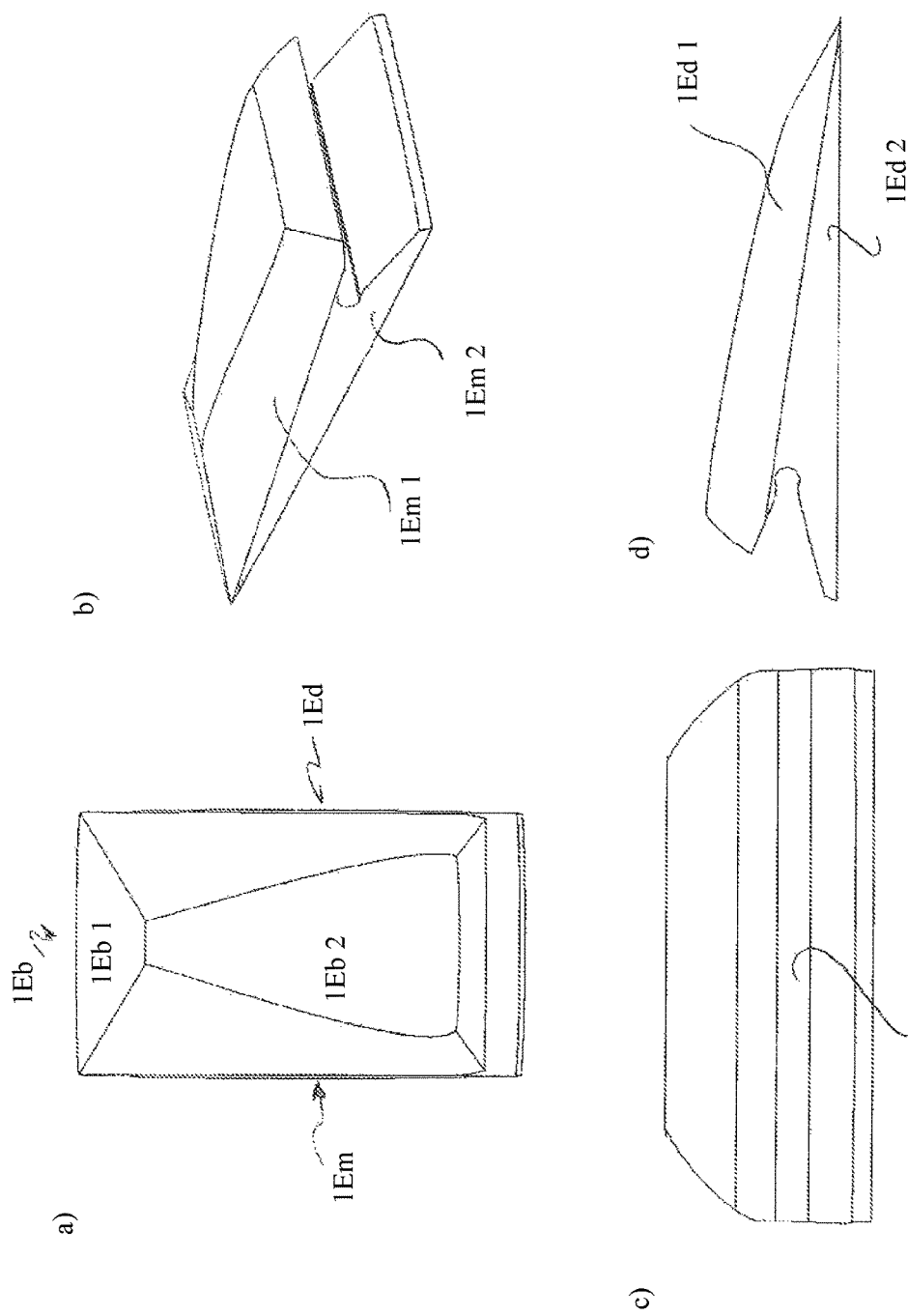

In FIG. 4 there is depicted in a) a top view, b) a perspective view, c) a first lateral view and d) a second lateral view of the guidance element 1 of FIG. 2 in a further embodiment. The embodiment of FIG. 4 differs from that of FIG. 2 in that the engagement surfaces 1E have a different shape: the buccal engagement surface 1Eb is divided into two sections 1Eb1, 1Eb2 which in turn run in an angle to one another in order to facilitate sliding-on of the treatment splint 5, see FIGS. 4*a*) and 4*c*). In the top view of FIG. 4*a*), the buccal sections 1Eb1, 1Eb2 are wedge-shaped with surface 1Eb1 extending the wedge-shape to the tooth connection surface 1T. Accordingly, the sections 1Em1, 1Ed1, too, are almost wedge-shaped in the top view of FIG. 4*a*).

Figure 5:
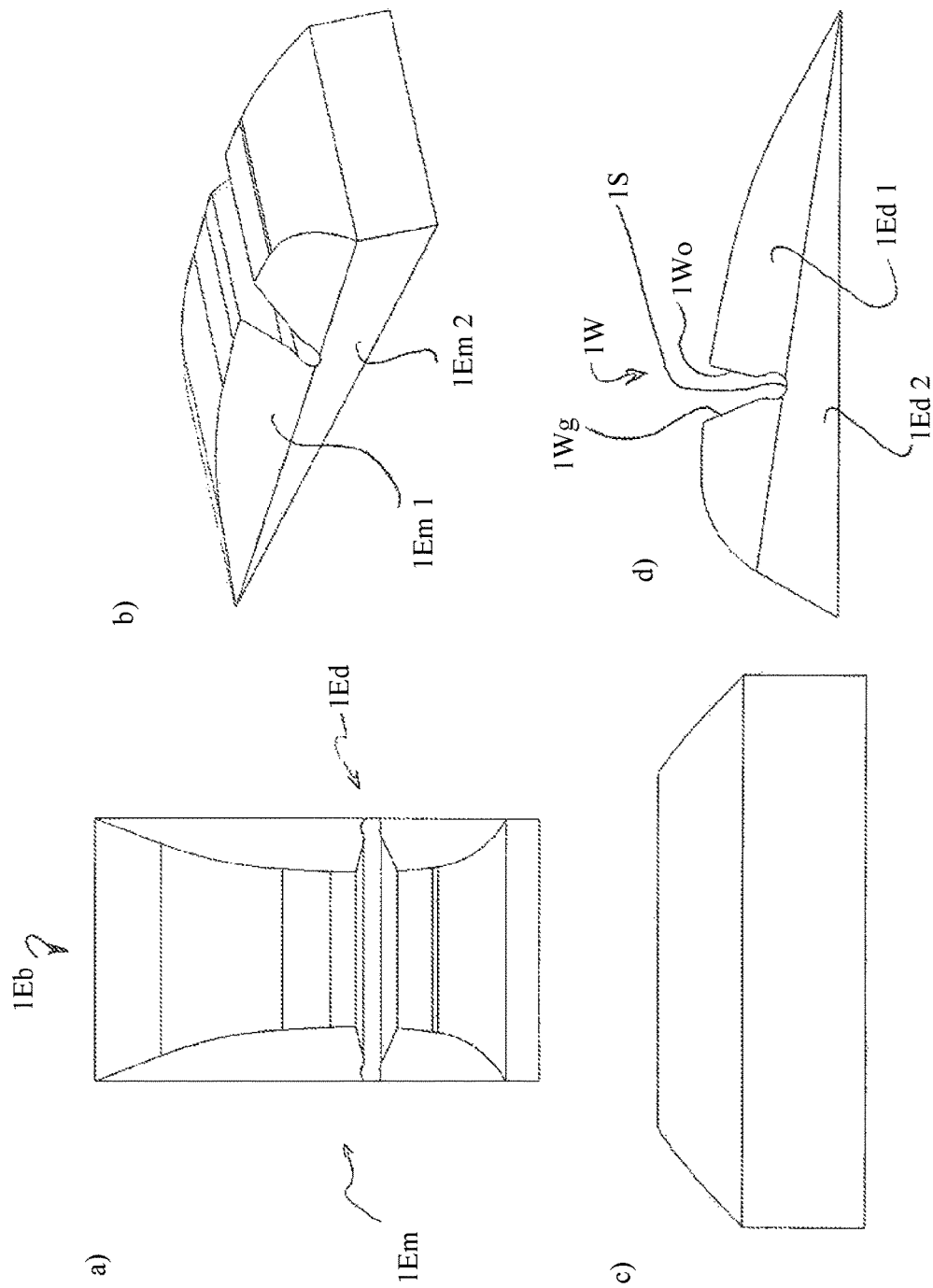

In FIG. 5 there is depicted in a) a top view, b) a perspective view, c) a first lateral view and d) a second lateral view of the guidance element 1 of FIG. 2 in a further embodiment. Again, the guidance element 1 has the buccal, mesial and distal engagement surfaces 1Eb, 1Em, 1Ed. Unlike the embodiment of FIG. 2, the guidance element 1 of FIG. 5 has a slot 1S which is arranged rather centrically in the longitudinal direction of the guidance element 1 and is accessible from buccal. A wire insertion region 1W has a gingival and an occlusal wire insertion surface 1Wg, 1Wo.

Figure 6:
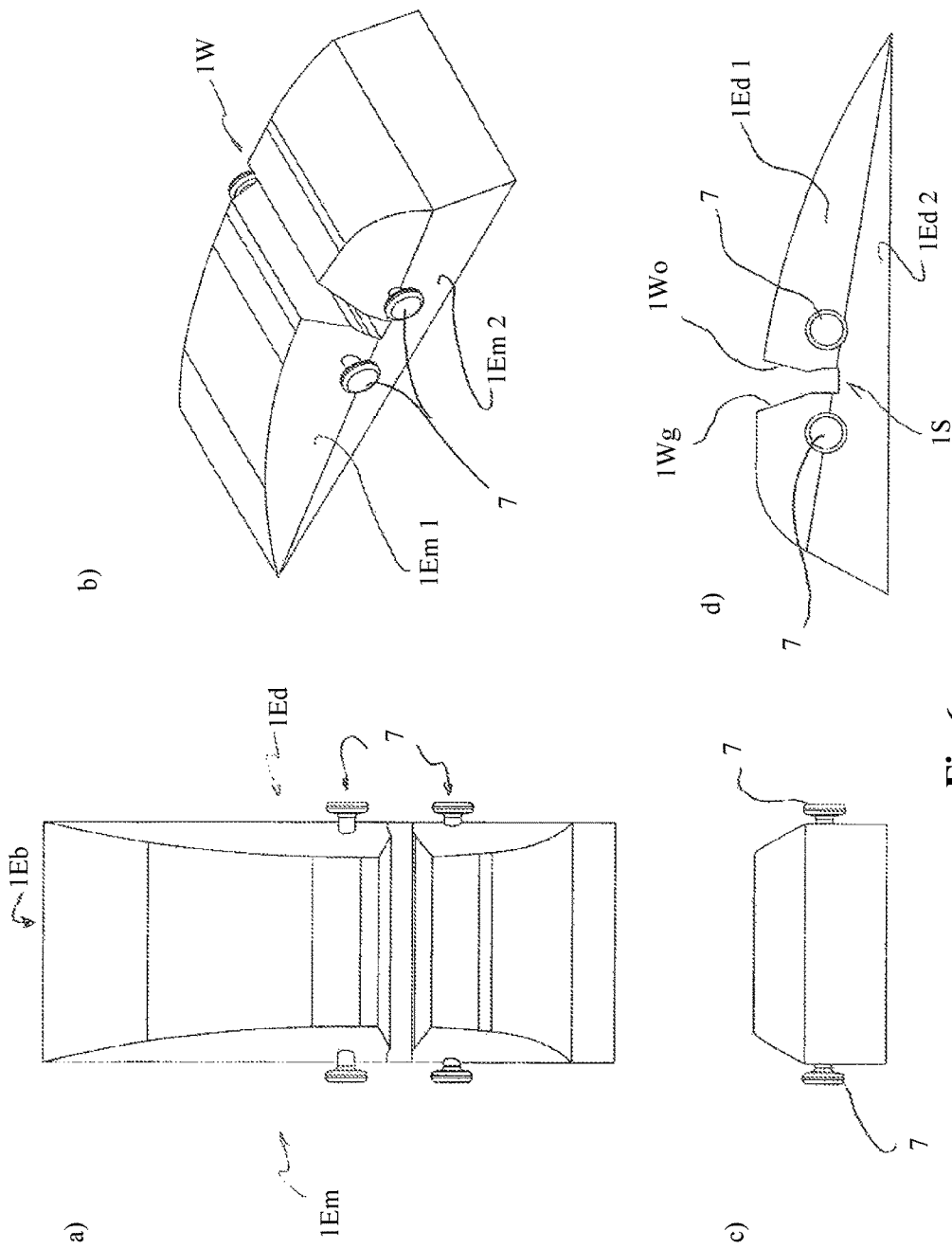

In FIG. 6 there is depicted in a) a top view, b) a perspective view, c) a first lateral view and d) a second lateral view of the guidance element 1 of FIG. 5 in a further embodiment. The guidance element 1 of FIG. 6 differs from that of FIG. 5 in that it has an almost square slot 1S. The gingival and occlusal wire insertion surfaces 1Wg, 1Wo remain unchanged.

A further difference are the mesially and distally arranged hooks 7 in order to ligate an orthodontic wire into the slot 1S with their assistance and with a ligation.

Figure 7:
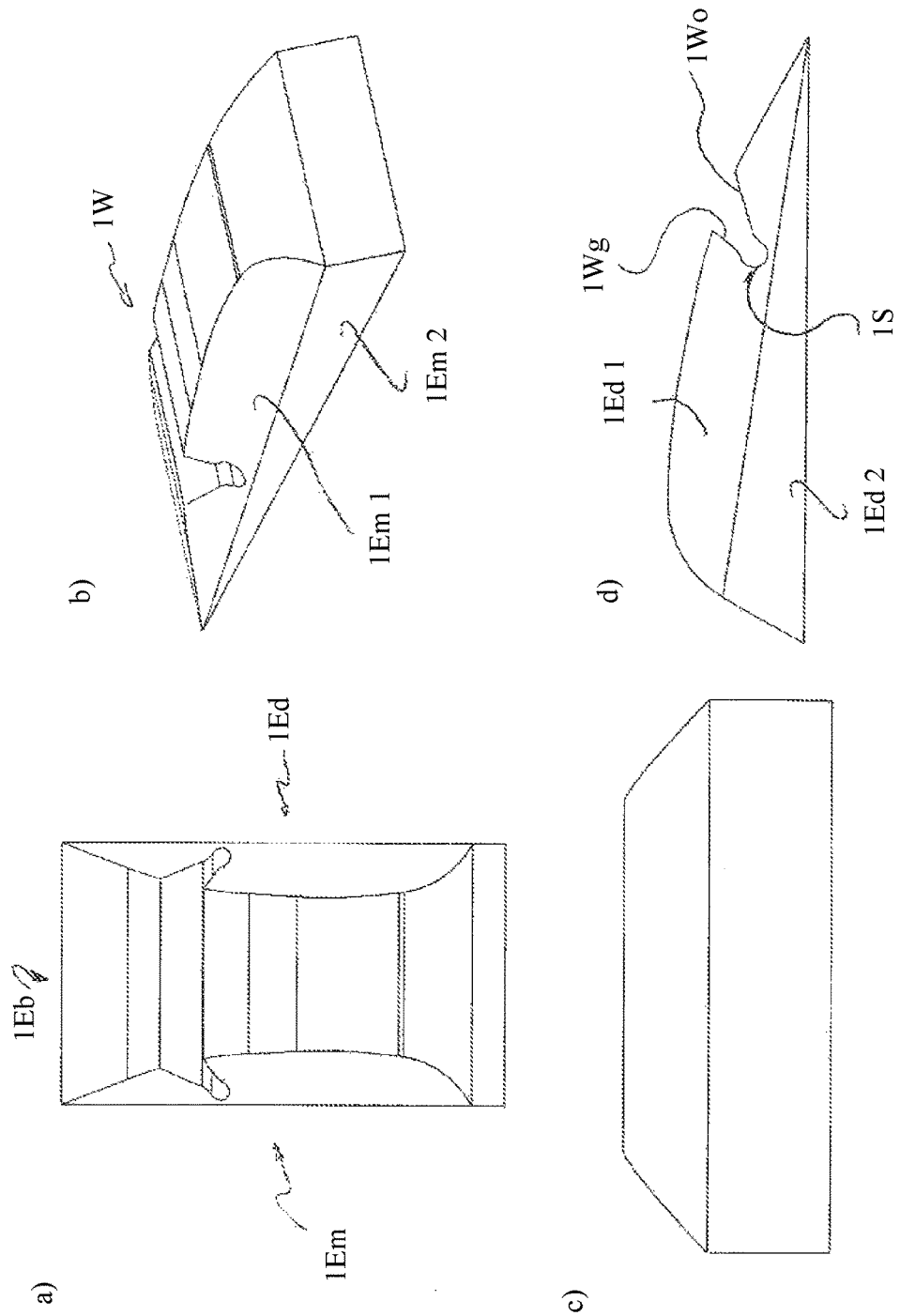

In FIG. 7 there is depicted in a) a top view, b) a perspective view, c) a first lateral view and d) a second lateral view of the guidance element 1 of FIG. 2 in a further embodiment. Again, the guidance element 1 has the buccal, mesial and distal engagement surfaces 1Eb, 1Em, 1Ed. Unlike in the embodiment of FIG. 2, the guidance element 1 of FIG. 7 has a slot 1S which is arranged rather occlusally in longitudinal direction of the guidance element 1 and is accessible from occlusal. A wire insertion region 1W has correspondingly inclined gingival and one occlusal wire insertion surfaces 1Wg, 1Wo.

Figure 8:
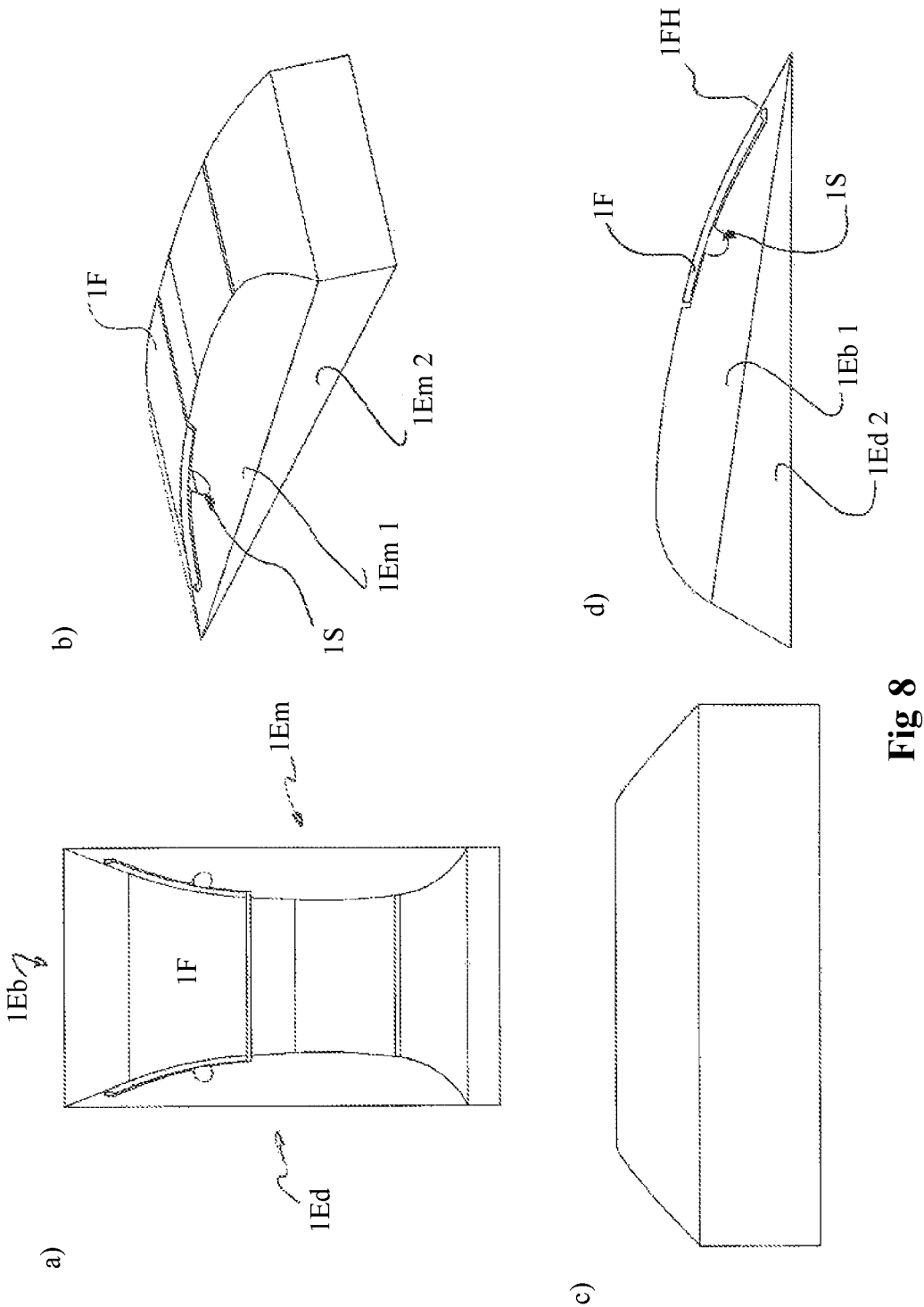

In FIG. 8 there is depicted in a) a top view, b) a perspective view, c) a first lateral view and d) a second lateral view of the guidance element 1 of FIG. 2 in a further embodiment. Again, the guidance element 1 has the buccal, mesial and distal engagement surfaces, 1Eb, 1Em, 1Ed.

Unlike FIG. 2, however, the slot 1S is arranged directly bucally such that the wire insertion region 1W is dispensed with. Further, the slot 1S is arranged behind a flap 1F which is formed integrally with the guidance element 1 and has a film hinge 1FH occlusally, whereby it is arranged articulatedly. In order to arrange a wire within the slot 1S, the flap 1F is lifted using a tool, for example a pair of pliers, and the wire is inserted into the slot 1S. Subsequently, the flap 1F is released again, whereby it resumes its initial position due to the reset force of the film hinge 1FH. Thus, a self-ligating guidance element 1 is produced.

Figure 9:
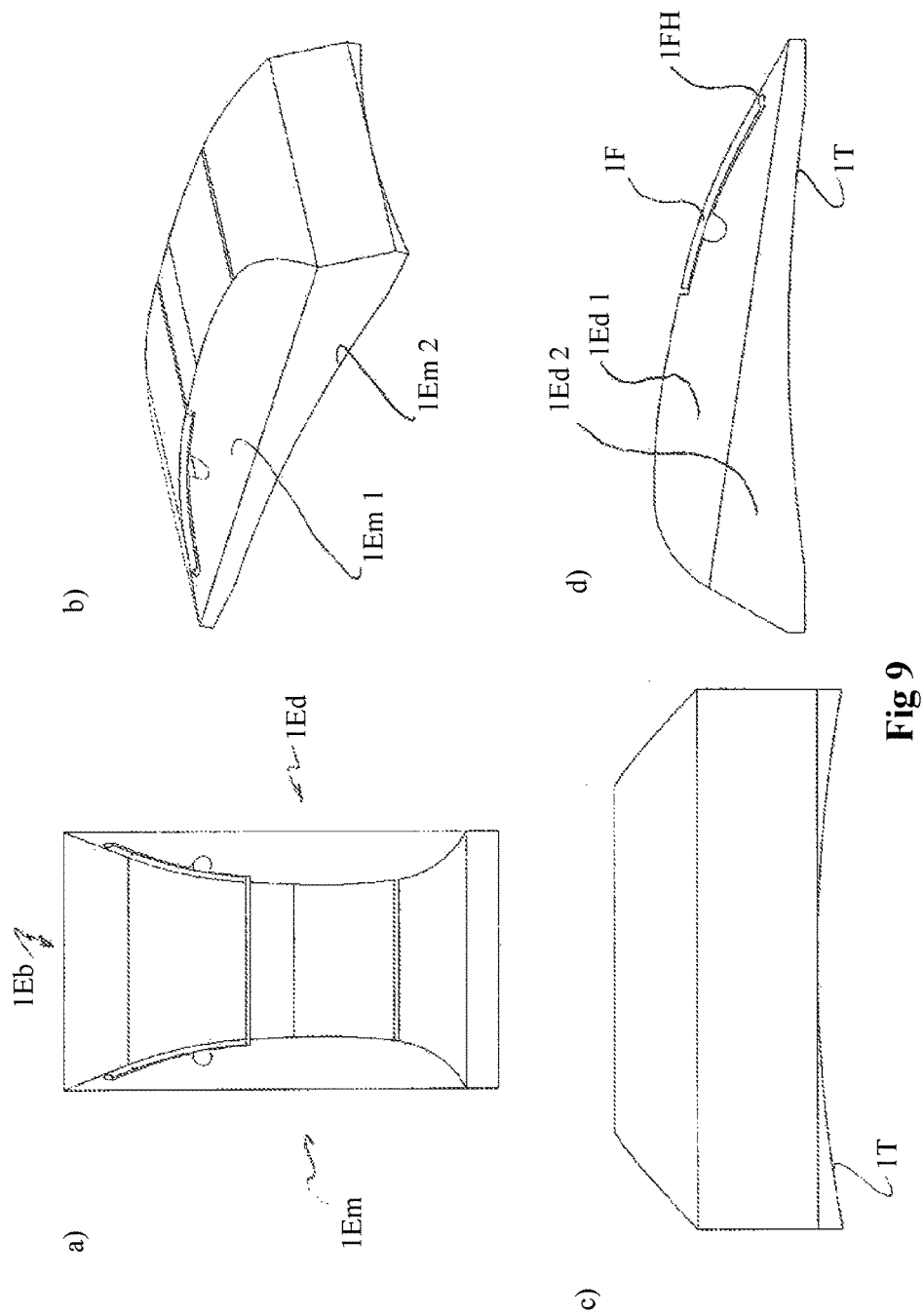

In FIG. 9 there is depicted in a) a top view, b) a perspective view, c) a first lateral view and d) a second lateral view of the guidance element 1 of FIG. 8 in a further embodiment. The guidance element 1 of FIG. 9 differs from that of FIG. 8 in that the tooth connection surface 1T is not planar but adapted to a tooth, in the present case to a 6th in the U. In FIG. 9*c*) a curvature of the tooth connection surface 1T around a gingival-occlusal axis is discernible. In FIG. 9*d*) a curvature of the tooth connection surface 1T around a mesio-distal axis is discernible.

Figure 10:
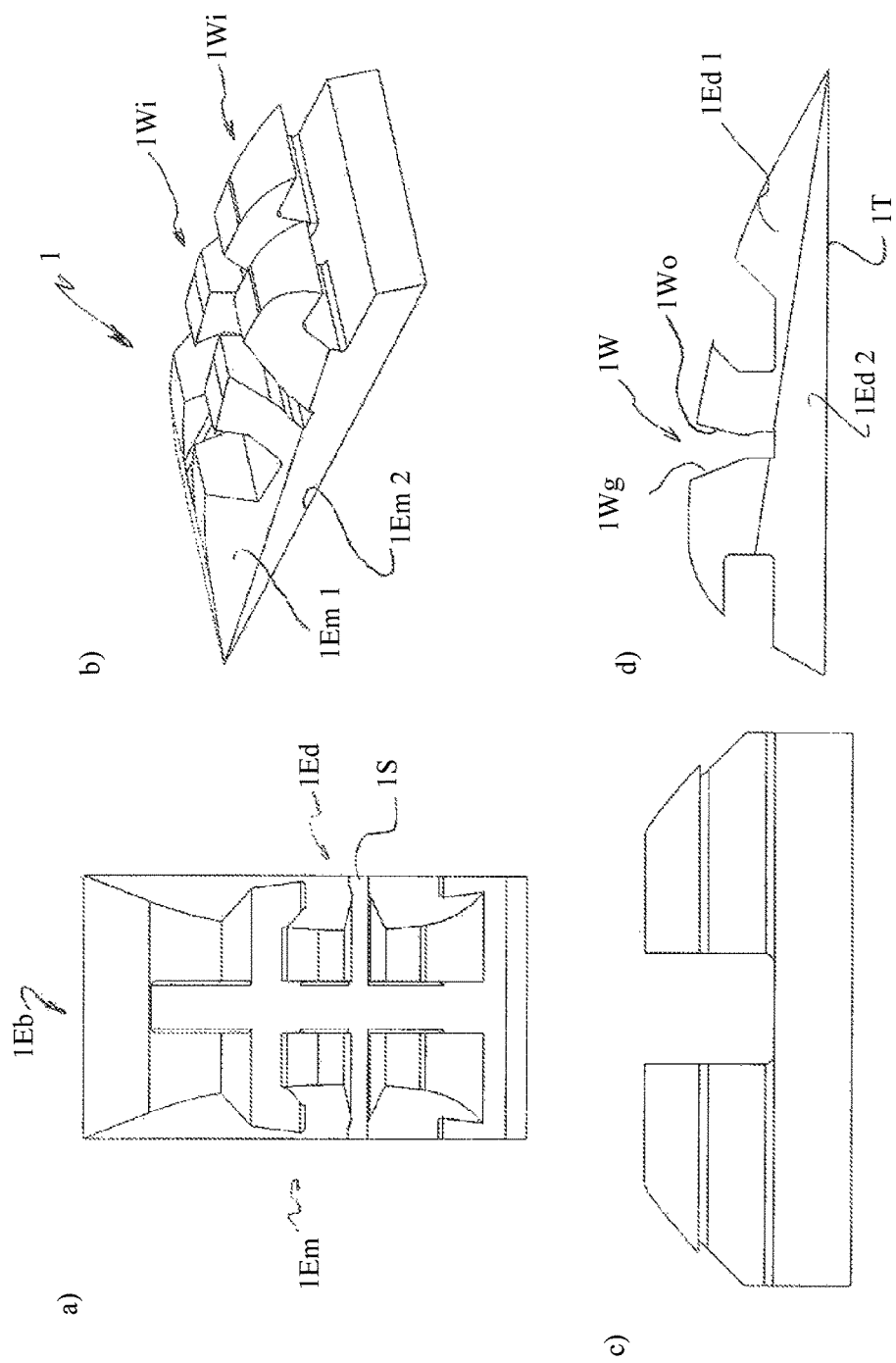

In FIG. 10 there is depicted in a) a top view, b) a perspective view, c) a first lateral view and d) a second lateral view of a guidance element 1 in a further embodiment. Again, the guidance element 1 has mesial, buccal and distal engagement surfaces 1Em, 1Eb, 1Ed and a slot 1S. The slot 1S has an almost square cross-section. A wire insertion region 1W having a gingival and an occlusal wire insertion surface 1Wg, 1Wo is assigned to the slot 1S. In order to be able to fix the wire within the slot 1S by means of ligations, four wings 1Wi are provided. Two wings 1Wi, respectively, are arranged gingivally and occlusally to the slot 1S. At the mesial and at the distal end of the guidance element 1 there are also arranged two wings 1Wi. After the insertion of a wire into the slot 1S it can be fixed within the slot 1S by means of the wings 1Wi using conventional ligations. In the example shown in FIG. 10 there are shown four essentially angular wings 1Wi. It is comprehensible that a differing number of wings 1Wi as well as different shapes of wings 1Wi and a different arrangement of the wings 1Wi can be chosen.

Figure 11:
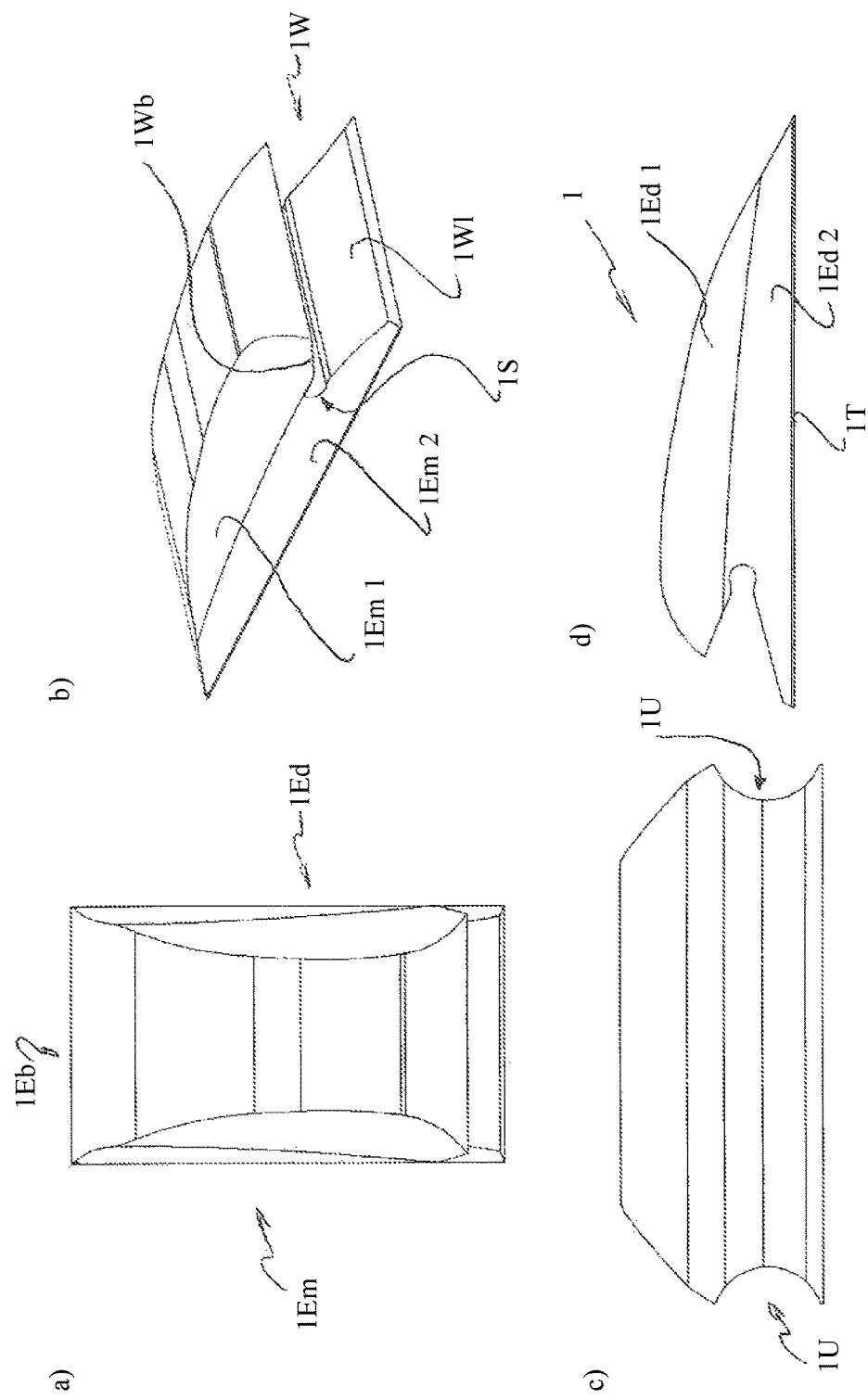

In FIG. 11 there is depicted in a) a top view, b) a perspective view, c) a first lateral view and d) a second lateral view of the guidance element 1 of FIG. 2 in a further embodiment. The embodiment of FIG. 11 differs from that of FIG. 2 in that an undercut 1U is formed in the mesial and in the distal engagement surfaces 1Em, 1Ed, respectively. The undercuts 1U serve for realizing a rubber band over several guidance elements 1 such that the rubber ring sectionally engages within the undercuts 1U and thus is held and fixed there, respectively.

Figure 12:
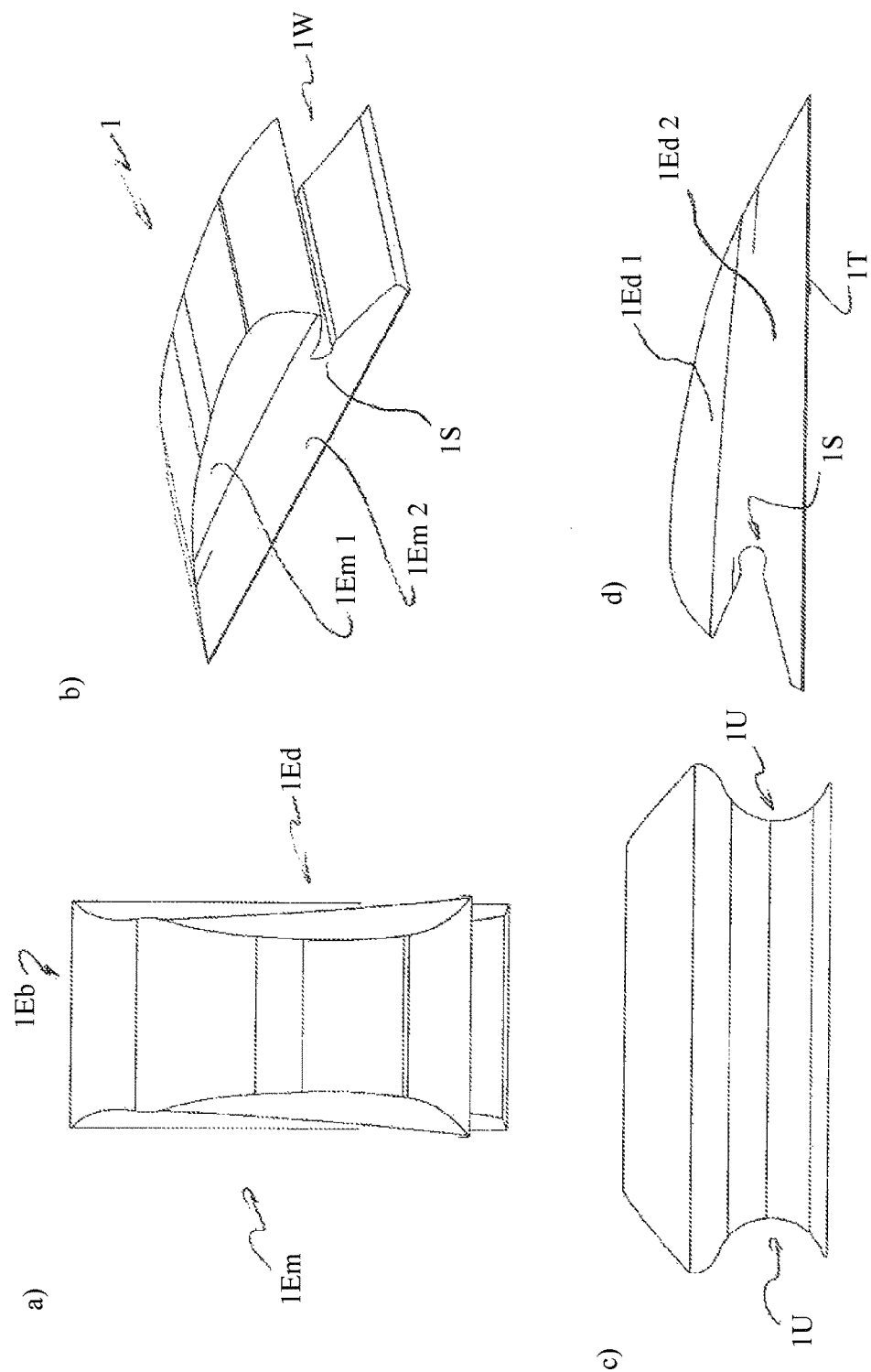

In FIG. 12 there is depicted in a) a top view, b) a perspective view, c) a first lateral view and d) a second lateral view of the guidance element 1 of FIG. 11 in a further embodiment. The embodiment of FIG. 12 differs from that of FIG. 11 in that the undercuts 1U are formed more pronounced in order to be able to also use rubber rings having a larger diameter and therefore a stronger fraction.

Figure 13:
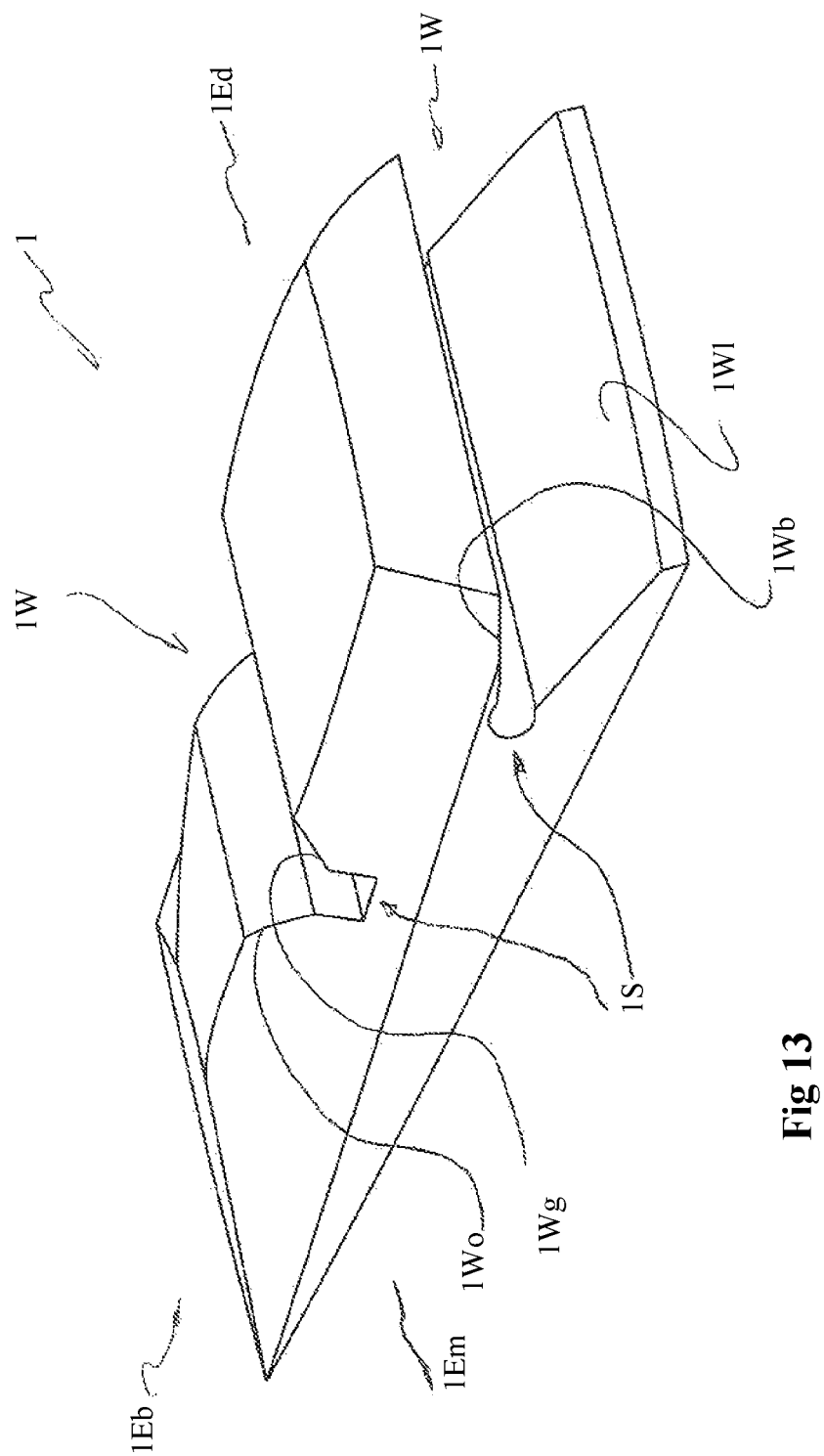

In FIG. 13 a further embodiment of a guidance element 1 is depicted which again has mesial, distal and buccal engagement surfaces 1Em, 1Ed, 1Eb. However, in contrast to the embodiments shown so far the guidance element 1 of FIG. 13 has two slots 1S, one of which is arranged buccally and one is arranged gingivally. There are each provided gingival and occlusal wire insertion surfaces 1Wg, 1Wo, and buccal and lingual wire insertion surfaces 1Wb, 1Wl, respectively. The buccal slot 1S has a square cross section, whereas the gingival slot 1S has a circular cross-section.

Figure 14:
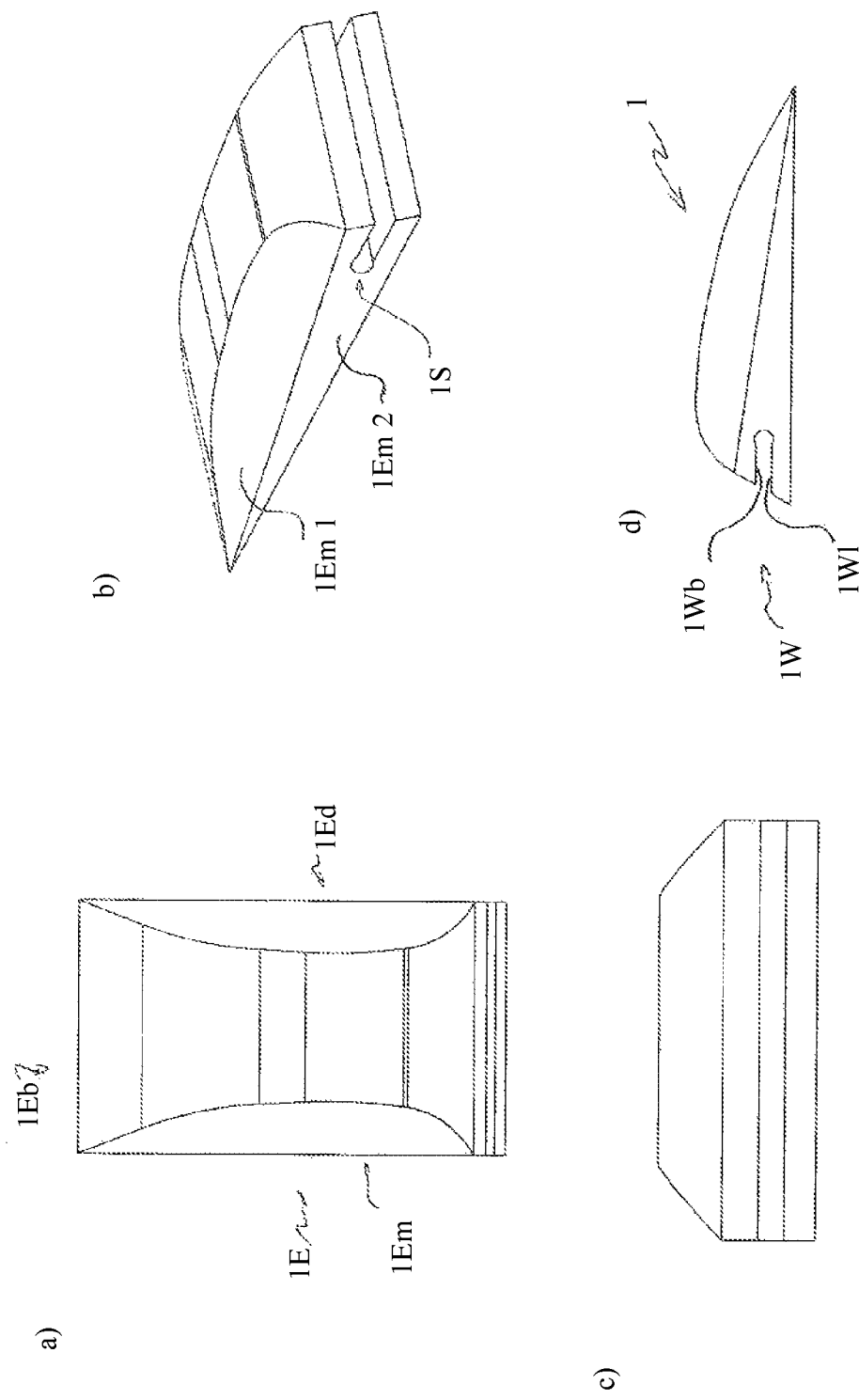

In FIG. 14 there is depicted in a) a top view, b) a perspective view, c) a first lateral view and d) a second lateral view of the guidance element 1 of FIG. 2 in a further embodiment. In contrast to the guidance element 1 of FIG. 2, the guidance element 1 of FIG. 14 has a self-ligating slot 1S. The slot 1S has a circular cross-section. There is provided a buccal and a lingual wire insertion surface 1Wb, 1Wl. An orthodontic wire is inserted into the slot 1S from gingival by shifting along the wire insertion surfaces 1Wb, 1Wl. The wire insertion surfaces 1Wb, 1Wl run almost in parallel to one another, alternatively they can run at an angle to one another, especially such that they run towards one another from gingival to occlusal. The distance of the wire insertion surfaces 1Wb, 1Wl to one another is dimensioned such that it is a little smaller than the diameter of the orthodontic wire and the modulus of elasticity of the material of the guidance element 1 is dimensioned to be smaller than that of the orthodontic wire. Thus, the orthodontic wire can be inserted into the slot 1S by manual application of force, but cannot disassociate itself from it, whereby the orthodontic wire is held within the slot 1S. For removal of the orthodontic wire from the slot 1S, it is removed from the guidance element 1 towards gingival along the wire insertion surfaces 1Wb, 1Wl by manual application of force.

In this embodiment the insertion of the orthodontic wire is achieved in that the guidance element 1 consists of a softer material than the orthodontic wire and in that the distance of the wire insertion surfaces 1Wb, 1Wl to one another is chosen accordingly. In a variant of this embodiment a suitable shaping instead of a softer material is chosen: the convex course of material above the buccal wire insertion surface 1Wb shown in FIG. 14d) in this variant assumes a concave course of material, i.e. it has a course of material running pointedly from a maximum from occlusal towards gingival, whereby an elastic lip is formed the lingual side of which forms the buccal wire insertion surface 1Wb. Upon insertion of the orthodontic wire this lip moves elastically towards buccal and the orthodontic wire can be inserted into the slot 1S, whereupon the elastic lip moves back to its initial position. For removal of the orthodontic wire from the slot 1S it is removed from the slot 1S and alongside of the wire insertion surfaces 1Wb, 1Wl upon pivoting of the lip towards buccal until the wire is outside of the guidance element 1, whereupon the lip moves back to its initial position.

Figure 15:
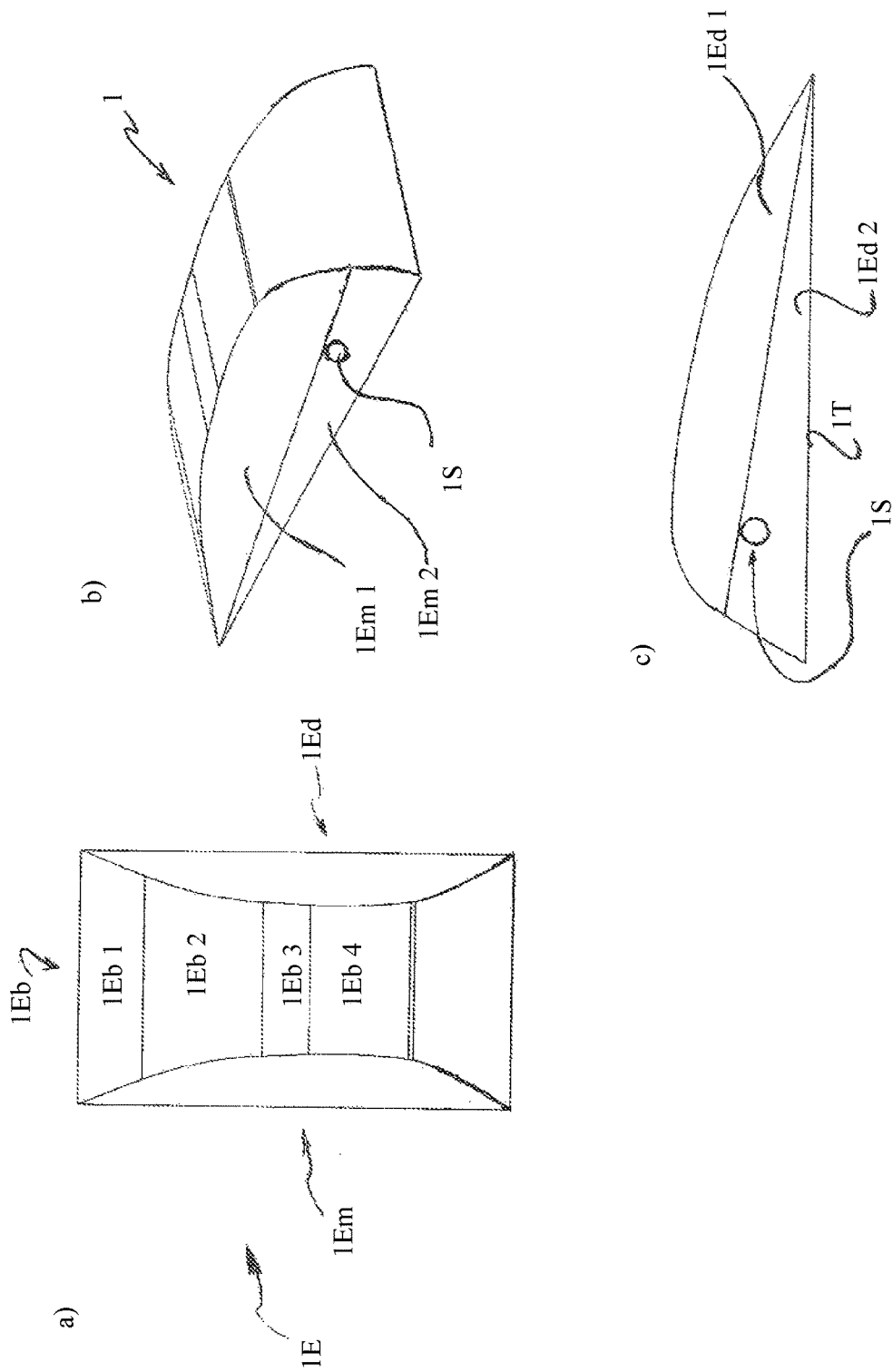

In FIG. 15 there is depicted in a) a top view, b) a perspective view, c) a lateral view of the guidance element 1 of FIG. 2 in a further embodiment. In contrast to the guidance element 1 of FIG. 2, the guidance element of FIG. 15 has no wire insertion region 1W. The slot 1S of the guidance element 1 of FIG. 15 lies completely within the guidance element 1. Thus, during a treatment an orthodontic wire is not inserted in buccal-lingual direction, but is inserted into the guidance element 1 in mesio-distal direction. Since with multiple guidance elements 1 in a jaw or with guidance elements 1 on adjoining teeth this way of inserting comes with a greater effort than with guidance elements 1 having ligations, the guidance elements 1 of FIG. 15 preferably are used as little as possible, for example only once or twice in one jaw, and for the rest for example guidance elements 1 according to FIGS. 2 to 14.

In the course of an orthodontic treatment the guidance elements 1 can be used in two ways: on the one hand a force can be exerted onto the teeth 3 assigned to the guidance elements 1 by the treatment splints 5 by means of the guidance elements 1 in order to achieve an orthodontic movement of the teeth 3. On the other hand an orthodontic treatment can take place by means of an orthodontic wire using the guidance elements 1 by arranging a wire within the slot 1S of the respective guidance element 1, as it is known with conventional brackets.

Therein the geometrical dimensions of the guidance elements 1 correspond to those that are present at known guidance elements for the aligner therapy. In particular the height of the same in lingual-buccal direction is smaller than 2 mm and preferably smaller than 1.5 mm.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

LIST OF REFERENCE NUMERALS 1 guidance element
1W wire insertion region
1Wb buccal wire insertion surface
1Wg gingival wire insertion surface
1Wl lingual wire insertion surface
1Wo occlusal wire insertion surface
1E engagement surface
1Eb buccal engagement surface
1Ed distal engagement surface
1Em mesial engagement surface
1Wi wing
1U undercut
1F flap
1FH film hinge
1S slot
1T tooth connection surface
3 tooth
5 orthodontic treatment splint
7 hook
UJ upper jaw
MP median plane

The invention claimed is:

1. An orthodontic system for a patient, comprising:
an orthodontic set, an orthodontic treatment splint, and an orthodontic treatment archwire; wherein the orthodontic set is configured for accepting either the orthodontic treatment splint or the orthodontic treatment archwire at different times so that treatment can be switched between treatment with the orthodontic treatment splint or the orthodontic treatment archwire; the orthodontic treatment splint defines a guidance pocket;
wherein the orthodontic set includes: at least two guidance elements, each is configured for attachment to a tooth of the patient; said at least two guidance elements each comprises a length, such that when attached to the tooth, said length defines a longitudinal axis extending along an occlusal-gingival direction; said at least two guidance elements each further comprises a continuous and uninterrupted tooth connection surface configured to be adapted to a surface of the tooth for the attachment to the tooth, and a buccal engagement surface divided into a first surface section (1Eb1), a second surface section (1Eb2), a third surface section (1Eb3), and a fourth surface section (1Eb4);
wherein the first, second, third, and fourth surface sections (1Eb1), (1Eb2), (1Eb3), and (1Eb4) each is at an angle to one another, and is opposite and facing away from the tooth connection surface, and is configured for positive engagement with the guiding pocket of the orthodontic treatment splint in order to exert orthodontic torques and/or forces onto the tooth during the positive engagement;
wherein the first surface section (1Eb1) is at a most occlusal portion of the buccal engagement surface, the second surface section (1Eb2) is gingivally adjacent to the first surface section (1Eb1), the third surface section (1Eb3) is gingivally adjacent to the second surface section (1Eb2), and the fourth surface section (1Eb4) is gingivally adjacent to the third surface section (1Eb3) and at a most gingival portion of the buccal engagement surface;
wherein the first surface section (1Eb1) and the third surface section (1Eb3) are flat; and the second surface section (1Eb2) and the fourth surface section (1Eb4) form a convex curve towards a buccal direction configured for sliding insertion of the orthodontic treatment splint onto and sliding removal of the orthodontic treatment splint from teeth having said at least two guidance elements attached thereon;
wherein the at least two guidance elements each having at least one slot, the at least one slot having a length perpendicular to the longitudinal axis and configured for reception of the orthodontic treatment archwire therein, wherein a wedge-shaped insertion region (1W) extends from the at least one slot towards an opening, said opening is configured for insertion of the orthodontic treatment archwire in a direction perpendicular to the length of the at least one slot; and wherein the wedge-shaped insertion region (1W) includes a buccal insertion surface (1Wb) and a lingual insertion surface (1W1) converging from the opening toward a narrowest site adjacent the at least one slot, wherein said narrowest site is configured to retain the orthodontic treatment archwire and prevent the orthodontic treatment archwire from disassociating itself from the at least one slot such that a manual application of gingivally directed force is required to remove the orthodontic treatment archwire from the at least one slot.

2. The orthodontic system according to claim 1, wherein said at least one slot comprising at least two slots.

3. The orthodontic system according to claim 1, wherein said at least one slot is self-ligating.

4. The orthodontic system according to claim 1, wherein said at least two guidance elements each at least partially consists of a ceramic material, a plastic material, a metal, or an alloy.

5. The orthodontic system according to claim 1, wherein said at least two guidance elements each further comprising a coating thereon.

6. The orthodontic system according to claim 5, wherein said coating is Teflon.

7. The orthodontic system according to claim 1, wherein the at least one slot has a circular, a square, a rectangular or polygonal shape in its cross-section.

8. The orthodontic system according to claim 1, wherein the at least one slot is arranged centrically, gingivally, or occlusally, in the occlusal-gingival direction.

9. The orthodontic system according to claim 1, wherein a shape and/or size of the tooth connection surface is adapted to a predefined tooth.

10. The orthodontic system according claim 1, wherein said at least two guidance elements each further comprising a hook, a wing, a knob, a tube, or an undercut.

11. The orthodontic system according to claim 1, wherein the orthodontic treatment splint is configured for an upper jaw or a lower jaw.

12. The orthodontic system according to claim 1, wherein the orthodontic system further comprises a plurality of said orthodontic treatment splints for the upper jaw and/or lower jaw.

13. The orthodontic system according to claim 1, wherein a plurality of guidance elements of said at least two guidance elements are configured to be simultaneously arranged on at least one same tooth in at least one treatment stage.

14. An orthodontic system for a patient, comprising:
an orthodontic set, an orthodontic treatment splint, and an orthodontic treatment archwire; the orthodontic set is configured for accepting either the orthodontic treatment splint or the orthodontic treatment archwire at different times so that treatment can be switched between treatment with the orthodontic treatment splint or with the orthodontic treatment archwire; the orthodontic treatment splint defines a guidance pocket;
wherein the orthodontic set includes: at least two guidance elements, each is configured for attachment to a tooth of the patient; said at least two guidance elements each comprises a length, such that when attached to the tooth, said length defines a longitudinal axis extending along an occlusal-gingival direction; said at least two guidance elements each further comprises: a continuous and uninterrupted tooth connection surface configured for attachment to a surface of the tooth, and a plurality of splint engagement surfaces each is opposite and facing away from the tooth connection surface;
wherein the plurality of splint engagement surfaces include a buccal surface (1Eb) and at least one of a distal, mesial, and/or gingival surfaces; said buccal surface and said at least one of a distal, mesial, and/or gingival surfaces are configured for positive engagement with the guidance pocket of the orthodontic treatment splint in order to exert orthodontic torques and/or forces onto the tooth during the positive engagement;
wherein the buccal surface (1Eb) is divided into a first surface section (1Eb1), a second surface section (1Eb2), a third surface section (1Eb3), and a fourth surface section (1Eb4), each is at an angle to one another; wherein the first surface section (1Eb1) is at a most occlusal portion of the buccal surface, the second surface section (1Eb2) is gingivally adjacent to the first surface section (1Eb1), the third surface section (1Eb3) is gingivally adjacent to the second surface section (1Eb2), and the fourth surface section (1Eb4) is gingivally adjacent to the third surface section (1Eb3) and at a most gingival portion of the buccal surface;

wherein the first surface section (1Eb1) and the third surface section (1Eb3) are flat; and the second surface section (1Eb2) and the fourth surface section (1Eb4) form a convex curve towards a buccal direction configured for sliding insertion and sliding removal of the treatment splint relative to teeth having said at least two guidance elements attached thereon;

wherein the at least two guidance elements each having at least one open slot with archwire insertion surfaces configured for reception and arranging of the orthodontic treatment archwire, wherein the at least one open slot is configured to retain the orthodontic treatment archwire and prevent the orthodontic treatment archwire from disassociating itself from the at least one open slot such that a manual application of gingivally directed force is required to remove the orthodontic treatment archwire from the at least one open slot.

15. The orthodontic system according to claim 14, said at least one open slot comprising at least two open slots.

16. The orthodontic system according to claim 14, wherein the at least one open slot is self-ligating.

17. The orthodontic system according to claim 14, wherein each of said at least two guidance elements at least partially consists of a ceramic material, a plastic material, a metal, or an alloy.

18. The orthodontic system according to claim 14, wherein each of said at least two guidance elements further comprising a coating thereon.

19. The orthodontic system according to claim 14, wherein said coating is Teflon.

20. The orthodontic system according to claim 14, wherein the at least one open slot comprises a circular, a square, a rectangular or polygonal shape in its cross-section.

21. The orthodontic system according to claim 14, wherein the at least one open slot is arranged centrically or gingivally or occlusally in the occlusal-gingival direction.

22. The orthodontic system according to claim 14, wherein the tooth connection surface is shaped and/or sized to be adapted to a predefined tooth.

23. The orthodontic system according claim 14, wherein each of said at least two guidance elements further comprising a hook, wing, knob, tube or an undercut.

24. The orthodontic system according to claim 14, wherein the orthodontic treatment splint is configured for an upper jaw or for a lower jaw.

25. The orthodontic system according to claim 14, wherein the orthodontic system further comprises a plurality of said orthodontic treatment splints for the upper jaw and/or lower jaw.

26. The orthodontic system according to claim 14, wherein a plurality of guidance elements of said at least two guidance elements are configured to be simultaneously arranged on at least one same tooth in at least one treatment stage.

27. An orthodontic system for a patient, comprising:
an orthodontic set, an orthodontic treatment splint, and an orthodontic treatment archwire; the orthodontic set is configured for accepting either the orthodontic treatment splint or the orthodontic treatment archwire at different times so that treatment can be switched between treatment with the orthodontic treatment splint or the orthodontic treatment archwire; the orthodontic treatment splint defines a guidance pocket;

wherein the orthodontic set includes: at least two guidance elements, each is configured for attachment to a tooth of the patient; said at least two guidance elements each comprises a length extending between an occlusal end and a gingival end thereof, such that when attached to the tooth, said occlusal and gingival ends are configured to be positioned toward a respective occlusal and gingival direction of the tooth; said at least two guidance elements each further comprises a continuous and uninterrupted tooth connection surface configured to be adapted to a surface of the tooth for the attachment to the tooth, and at least one buccal engagement surface divided into several surface sections each being opposite and facing away from the tooth connection surface and configured for positive engagement with the guidance pocket of the orthodontic treatment splint in order to exert orthodontic torques and/or forces onto the tooth;

wherein the several surface sections include a first buccal surface section (1Eb1) and a second buccal surface section (1Eb2) running at an angle to one another; wherein the first buccal surface section (1Eb1) is adjacent the occlusal end, and the second buccal surface section (1Eb2) is gingivally adjacent to the first buccal surface section (1Eb1); wherein the first buccal surface section (1Eb1) and the second buccal surface section (1Eb2) taper toward the occlusal end such as to form a wedge-shaped portion with a converging wedge edge at the occlusal end and extending between the first surface section (1Eb1) and the tooth connection surface for sliding insertion and sliding removal of the orthodontic treatment splint from teeth having said at least two guidance elements attached thereon; and wherein the at least two guidance elements each having at least one slot configured for reception and arranging of the orthodontic treatment archwire, wherein the at least one slot is configured to hold the orthodontic treatment archwire and prevent the orthodontic treatment archwire from disassociating itself from the at least one slot such that a manual application of gingivally directed force is required to remove the orthodontic treatment archwire from the at least one slot.

28. An orthodontic system for a patient, comprising:
an orthodontic set, an orthodontic treatment splint, and an orthodontic treatment archwire; the orthodontic set is configured for accepting either the orthodontic treatment splint or the orthodontic treatment archwire at different times so that treatment can be switched between treatment with the at least one orthodontic treatment splint or the orthodontic treatment archwire; the orthodontic treatment splint defines a guidance pocket;

wherein the orthodontic set includes: at least two guidance elements, each is configured for attachment to a tooth of the patient; said at least two guidance elements each comprises a length, such that when attached to the tooth, said length defines a longitudinal axis extending along an occlusal-gingival direction; said at least two guidance elements each further comprises a continuous and uninterrupted tooth connection surface configured to be adapted to a surface of the tooth for the attachment to the tooth, and a plurality of splint engaging surfaces each being opposite the tooth connection surface and facing away from the tooth connection surface;

wherein the plurality of splint engaging surfaces comprises a buccal or lingual engagement surface (1Eb) and at least one of a distal, mesial, and/or a gingival surface;

wherein said buccal or lingual engagement surface and said at least one of the distal, mesial, and/or gingival surface each is configured for positive engagement with the guidance pocket of the orthodontic treatment splint in order to exert orthodontic torques and/or forces onto the tooth during the positive engagement;

wherein the buccal or lingual engagement surface (1Eb) is divided into at least a first surface section (1Eb1) and a second surface section (1Eb2) angled relative to each other; wherein the first surface section (1Eb1) is at a most occlusal portion of the buccal engagement surface (1Eb) and tapers toward an occlusal end of the buccal or lingual engagement surface (1Eb) such as to form a tapering wedge-shaped portion with a wedge-shaped end edge being the occlusal end extending between the first surface section (1Eb1) and the tooth connection surface for sliding insertion and sliding removal of the orthodontic treatment splint from teeth having said at least two guidance elements attached thereon;

wherein the at least two guidance elements each having at least one slot configured for reception and arranging of the orthodontic treatment archwire, wherein the at least one slot is configured to hold the orthodontic treatment archwire and prevent the orthodontic treatment archwire from disassociating itself from the at least one slot such that a manual application of gingivally directed force is required to remove the orthodontic treatment archwire from the at least one slot.

* * * * *